United States Patent [19]

O'Brien

[11] 4,352,781
[45] Oct. 5, 1982

[54] COMBUSTION SYSTEM

[75] Inventor: Larry O'Brien, St. Joseph, Mich.

[73] Assignee: Leco Corporation, St. Joseph, Mich.

[21] Appl. No.: 196,781

[22] Filed: Oct. 14, 1980

[51] Int. Cl.³ ............................................. G01N 31/12
[52] U.S. Cl. ....................................... 422/78; 422/102
[58] Field of Search ................................. 422/78, 102

[56] References Cited
U.S. PATENT DOCUMENTS 3,985,505 10/1976 Bredeweg ............................ 422/78
4,234,541 11/1980 Bredeweg et al. ................... 422/78
4,282,183 8/1981 Bredeweg et al. ................... 422/78

Primary Examiner—Peter Chin
Attorney, Agent, or Firm—Price, Heneveld, Huizenga & Cooper

[57] ABSTRACT

A combustion system includes a cylindrical horizontally extending ceramic combustion tube enclosed at one end and open at the opposite end for receiving a combustion boat carrying a sample to be combusted for subsequent analysis. An externally mounted sample eduction tube is coupled at one end to the interior space near the enclosed end of the combustion tube and secured at its opposite end to the combustion tube by means of a slide assembly to accommodate for differential movement between the combustion tube and the eduction tube. A lance tube also extends into the combustion tube for directing the flow of an oxidizing gas into the combustion boat to facilitate oxidation of a sample. The open end of the combustion tube is effectively sealed by a curtain of gas supplied by a flood tube for blocking the open end of the tube from admission of atmospheric contaminants and preventing the escape of gases from the combusted sample. A baffle structure is positioned between the combustion boat and gas exit to contain volatile samples during combustion.

12 Claims, 6 Drawing Figures

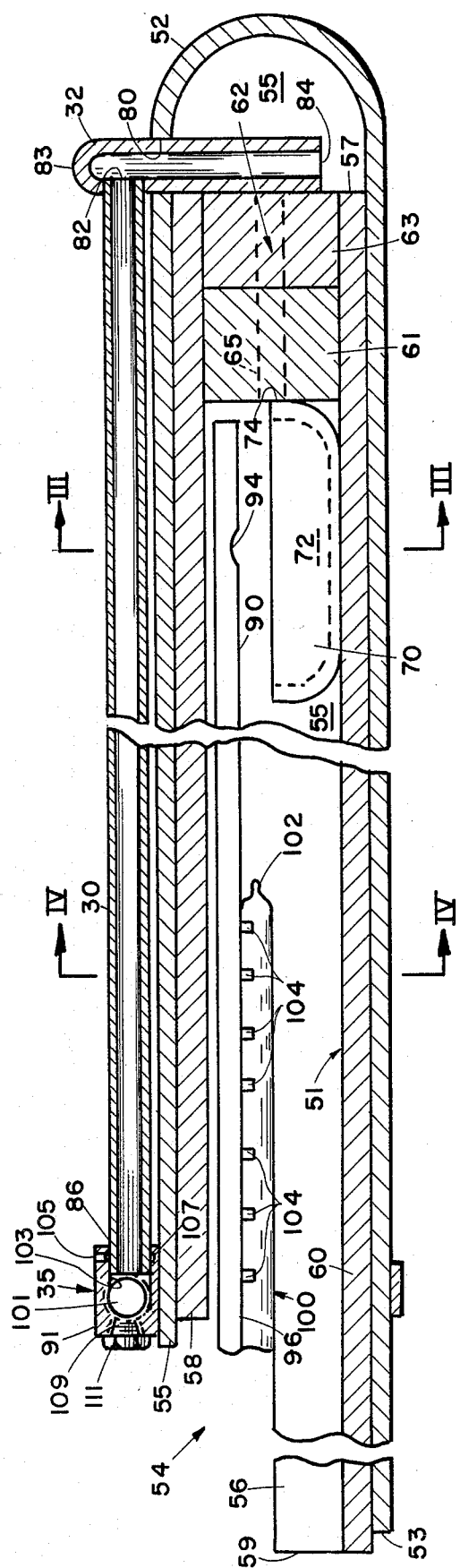
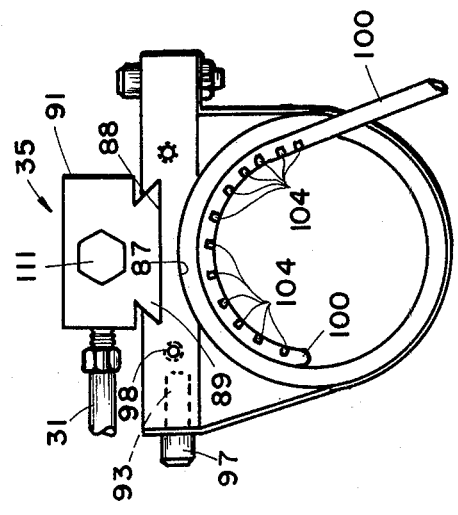
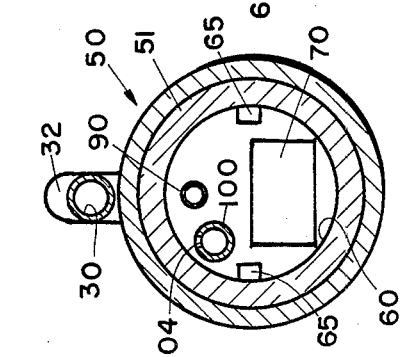
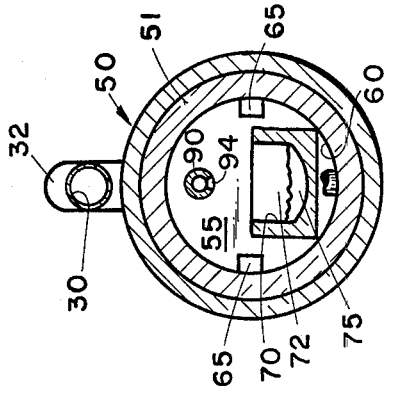
FIG 2
FIG 5
FIG 6
FIG 4
FIG 3

COMBUSTION SYSTEM

BACKGROUND OF THE INVENTION

The present invention relates to combustion systems and particularly to an improved system for use in combusting a solid or liquid specimen to a gaseous sample for subsequent analysis.

In existing analyzers such as Model No. IR-33 sulphur determinator, commercially available from Leco Corporation of St. Joseph, Mich., the sulphur content of coal, coke, or other substances can be determined from a solid or liquid specimen which is positioned in an induction furnace and combusted to provide a gaseous sample. The gaseous sample is subsequently analyzed by an infrared detector detecting the sulphur dioxide concentration which is then displayed by a digital display as the sulphur content of the specimen. Certain aspects of the combustion system used in such prior art is disclosed in U.S. Pat. No. 3,923,464, issued Dec. 2, 1975, to Sitek, et al, and assigned to the present assignee.

Such systems are open ended and employ a carrier gas introduced into the combustion chamber of the induction furnace to oxidize the specimen and carry the resultant specimen gases through the opposite end of the combustion chamber and through an infrared cell for detection. A closed loop combustion system of this general type is described in U.S. Pat. No. 3,985,505, issued Oct. 12, 1976, to R. L. Bredeweg, and assigned to the present assignee.

Although these systems provide excellent results in analyzing a specimen, coal cannot be heated directly with radio frequency energy used in these devices since it is a nonconductor. As a result, accelerating agents such as iron chips or powder or tungsten are required to be added to the sample. Further, the combustion chamber in such systems is relatively small and due to the fact that the coal is naturally combustible and creates an exothermic reaction during its combustion, it tends to sputter and some of the specimen can easily escape from the hot zone of the combustion chamber and not be broken down to provide an accurate analysis.

U.S. patent application Ser. No. 958,967 filed on Nov. 9, 1978, entitled Combustion System discloses an improved closed end combustion chamber having a relatively large hot zone and an open end for receiving a combustion boat containing the specimen to be analyzed and an enclosed opposite end. The specimen gas is withdrawn from near the closed end of the combustion chamber by an eduction tube extending within the combustion chamber and the open end of the combustion chamber is effectively sealed by a gas curtain such that the interior of the chamber is available to the operator for readily inserting and removing specimens for combustion.

Although the enclosed combustion tube provides a significant improvement over the prior art it was discovered that on occasion, the floating end of the tube would fuse to its support block and differential movement in the order of 0.001 to 0.030 inches between the eduction tube and the combustion tube due to longitudinal expansion or contraction with temperature changes, warpage, and aging caused the eduction tube to fracture due in part to its relatively small size and therefore its fragility. Inasmuch as the eduction tube is anchored at one end to the combustion chamber and the free end could become fused to the spacing block employed in connection with the combustion system, such differential movement could not always be accommodated causing fracture of the eduction tube.

Also, it was discovered that with some highly volatile specimens, undesired ash, or other combustion by-products would, due to their vigorous combustion, fly from the combustion boat and tend to clog the eduction tube.

SUMMARY OF THE PRESENT INVENTION

The system of the present invention overcomes the difficulties encountered with the prior art by providing an externally mounted eduction tube positioned to extend closely adjacent and parallel to the exterior of the combustion tube and including means for coupling one end of the eduction tube to communicate with the interior space of the combustion chamber near the enclosed end thereof. The opposite end of the eduction tube is secured to the combustion tube by longitudinally slideable means such that differential motion in a longitudinal direction between the combustion tube and the eduction tube can be accommodated by the sliding mounting means. In one embodiment of the invention, improved baffle means are provided to control highly volatile samples in the combustion zone.

These and other features, advantages and objects of the present invention can best be understood by reference to the following description thereof, together with the drawings, in which:

BRIEF DESCRIPTION OF THE DRAWINGS

FIG. 2 is a side elevational view partly in cross section of a combustion chamber embodying the present invention;

FIG. 3 is a cross-sectional view of the combustion chamber taken along the section lines III—III of FIG. 2;

FIG. 4 is a cross-sectional view of the combustion chamber taken along section lines IV—IV of FIG. 2;

FIG. 5 is an enlarged front elevational view of the slide assembly shown also in FIG. 2; and FIG. 6 is a front elevational view of the baffle structure shown in FIG. 2.

DETAILED DESCRIPTION OF THE PREFERRED EMBODIMENT

Figure 1:
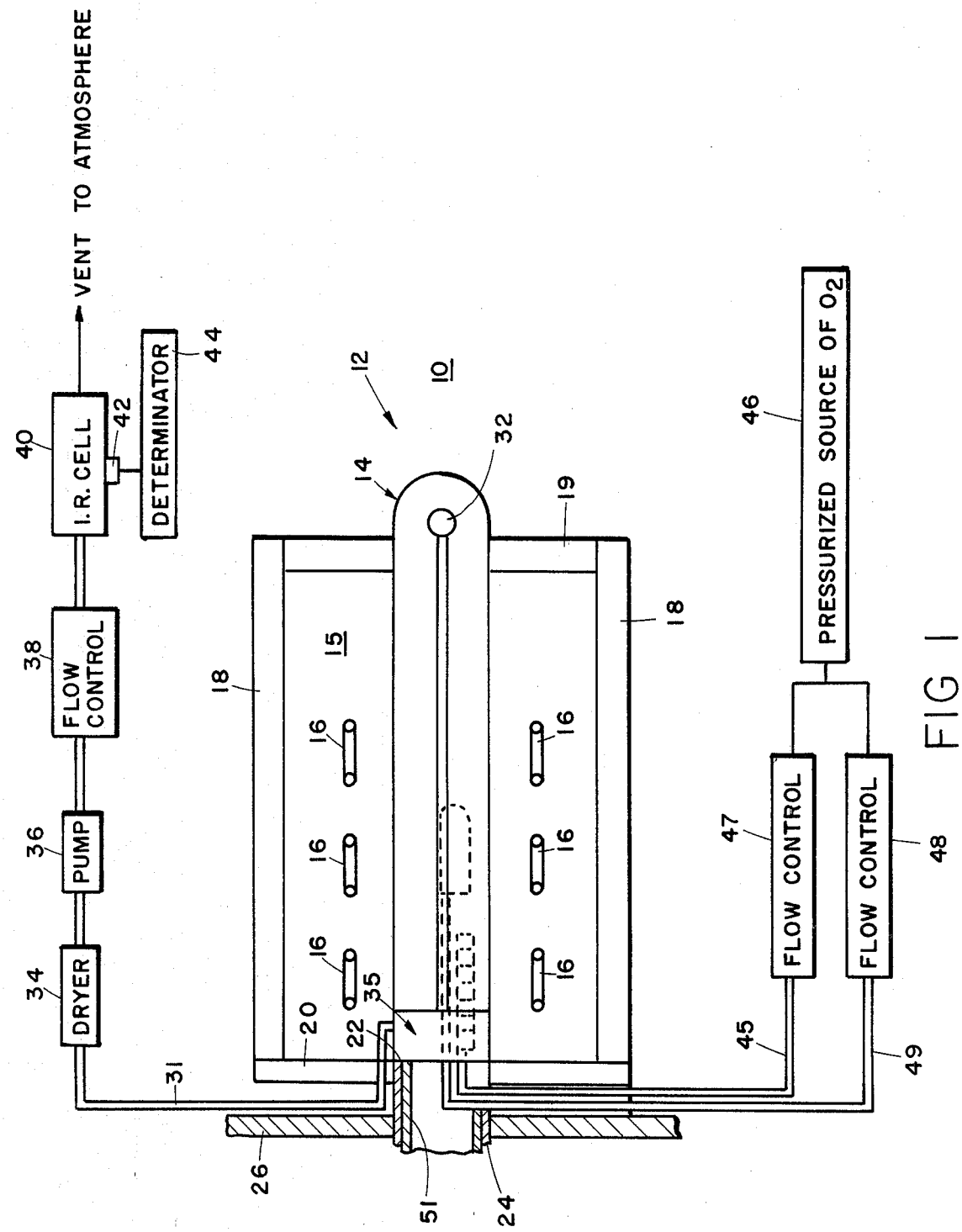
FIG. 1 is an analyzer incorporating the combustion system of the present invention shown partly in schematic and block diagram form.

Referring initially to FIG. 1, there is shown an analyzer 10 which, in the preferred embodiment, is employed for determining the percentage sulphur content in coal and coke. Although the preferred embodiment is used with these solid materials which are pulverized into powder form for combustion, it is to be understood that the combustion apparatus of the present invention can be used with other solid or liquid materials and for determining other constituent elements of a given specimen.

The analyzer 10 comprises a combustion furnace 12 shown in top plan view partly broken away in FIG. 1 and including a combustion chamber 14 positioned within the furnace. Furnace 12 is a resistance type furnace having six generally U-shaped resistance heating elements 16, three of which are positioned adjacent and on opposite sides of the combustion chamber 14. The heating elements and combustion chamber are housed within a refractory box including sidewalls 18, a rear wall 19, and a front wall 20 having an access opening 22 for the extension of one end of the combustion chamber through an access port 24 in the instrument's front panel 26. The chamber extends slightly through and is supported at one end by wall 19 as seen in FIG. 1. The refractory lining of the furnace 12 also includes a floor 15 and a top (not shown in the drawing). Thus, the combustion chamber 14 is totally enclosed within the resistance furnace 12. The resistance heating elements 16 are preferably KANTHAL ® type resistance elements made of molybdenum disilicide and provide heating temperatures to the interior of the combustion chamber 14 in excess of 2000° F. with the maximum temperature being in the neighborhood of 2800° F.

Gases from the specimens being combusted within the combustion chamber are withdrawn by an eduction tube 30 which, as described in greater detail below, extends closely adjacent to and along the outside of combustion chamber 14 and is coupled at one end with an exit fitting 32 communicating with the interior of the combustion chamber and is slideably mounted at its opposite end to the combustion chamber by means of a slide assembly 35. The eduction tube 30 is coupled by a conduit 31 to an anhydrous dryer 34 for removing water from the specimen gas. The output of dryer 34 is coupled to the input of a pump 36 for drawing the specimen gas through the dryer and from the combustion chamber 14 through the eduction tube 30. The output of the pump 36 is coupled to a flow control 38 for providing a flow rate of approximately three liters per minute to the input of an IR cell 40. The output of IR cell 40 is vented to the atmosphere.

IR cell 40 includes a detector 42 which is electrically coupled to a determinator 44 including electrical circuits for processing the electrical signals from detector 42 and providing a digital readout of the percentage of sulphur content in the specimen being combusted. The determinator 44, elements 34 through 44 are of a construction which can be of the type disclosed in the above identified U.S. Pat. No. 3,985,505, the disclosure of which is incorporated herein by reference. Naturally, modifications to the specific electrical circuitry can be made to accommodate the system for the particular specimen gas being analyzed. In the preferred embodiment, the IR cell includes an SO filter for the detection of sulphur dioxide which is the combination of the element sulphur and the oxidizing gas oxygen employed in the system of the preferred embodiment.

The analyzer further includes a pressurized source 46 of oxygen gas coupled to a pair of rotometers 47 and 48 which supply the oxidizing as to the combustion chamber 14 by supply conduits 45 and 49, respectively. Thus, the specimen material is combusted by the furnace 12 in the presence of oxygen to convert the sulphur contained within the specimen to sulphur dioxide for subsequent analysis. Having briefly described the overall environment of the combustion system of the present invention, a detailed description of the combustion chamber 14 and associated improvements is now presented in conjunction with FIGS. 2 through 4.

As seen in FIGS. 2 through 4, the combustion chamber 14 embodying the present invention includes a tube 50 of generally cylindrical construction and having a rounded continuously closed first end 52 and an opposite continuously open second end 54. In FIG. 2 tube 50 itself is shown in cross section so as to clearly illustrate the relative position of the various elements of the system. The cylindrical combustion tube 50 is made of relatively thin wall construction and has an inside diameter of approximately 1½ inches with a wall thickness of ⅛ inch. In the preferred embodiment, the combustion tube is made of a ceramic material such as alumina. It could also be made of other suitable refractory material capable of withstanding temperatures of in excess of about 2800° F. The tube includes a cutaway segment near the open end to define a pair of generally horizontally extending surfaces 56 (FIG. 2) which extend outwardly from open end 54 a distance of about 2.25 inches. The notch formed by cutting away an upper curved one half segment of the open end of tube 50 also defines semiannular end walls 53 and 55. The overall length of the combustion tube of the preferred embodiment from wall 53 to end 52 is 18.12 inches. In the construction of the combustion tube, it is desired to keep the length of the tube significantly greater than its diameter so that a relatively long hot zone within the furnace shown in FIG. 1 is provided and the interior of the tube can be effectively sealed using a curtain of gas. Thus, the length to internal diameter ratio of the tube of the preferred embodiment is slightly greater than 12:1.

The combustion chamber also includes a zircon liner 51 which in the preferred embodiment is cylindrical and has an outer diameter slightly smaller than the inner diameter of the combustion tube 50. This permits the zircon liner to easily be fitted within the combustion tube for protecting the combustion tube from the by-products of combustion and from thermal shock. The zircon lining can be replaced periodically thereby greatly extending the life of the combustion tube itself. Liner 51 has an open cylindrical end extending into contact with an exit fitting 32 as seen in FIG. 2. The wall thickness of zircon lining 51 is approximately 50% greater than the wall thicknesses of the combustion tube and its end opposite end 57 is cut away in a manner similar to the combustion tube to define semiannular surfaces 58 and 59 with surface 58 extending inwardly from the surface 55 of the combustion tube and surface 59 extending slightly outwardly from the end 53 of the combustion tube so as to provide a smooth floor for insertion of a combustion boat 70 on the floor of liner 51.

Combustion tube 50 is adapted to be oriented horizontally within furnace 12 and as such the lower half of the cylindrical interior wall of the liner 51 defines a floor 60 which slideably receives a rod-shaped ceramic baffle 62 positioned between the combustion boat 70 and gas exit 32. Baffle 62 is formed in two segments 61 and 63 positioned longitudinally against one another and including, as best seen in FIG. 6, a pair of longitudinally extending aperture means comprising rectangular channels 65 spaced at 180° intervals.

Each of the blocks 61 and 63 forming the baffle means 62 is made of alumina having a porosity in the range of 10 to 15%. The two sections 61 and 63 can be rotated relative to one another to provide a selectively restricted flow path comprising the channels 65 for gases flowing from the combustion boat 74 to the open lower end of inlet 32. Thus, for example, by aligning the channels 65 of block 61 with channels 65 of block 63, a maximum flow path is achieved. By rotating one or both of the blocks however the channels can be selectively misaligned to selectively restrict the flowpath. This is desirable in some instances where highly volatile substances such as peat samples or highly volatile coal are being analyzed and tend to sputter out of the combustion zone. The baffle 62 acts as a shield for trapping said combustion by-products as ash and parts of the sample itself thereby confining such samples and material to the combustion area during combustion and assuring complete combustion. Segments 61 and 63 can be rotatably adjusted by using a suitable wire rod typically inserted in one of the channels 65 of segment 61. The diameter of segments 61 and 63 is slightly less than the inner diameter of liner 51 and rests on the floor thereof. Baffle 62 functions also to position a combustion boat 70 in the combustion zone in longitudinally spaced relationship with respect to the first end 52 of the combustion tube 50.

The eduction tube 30 is secured at one end to an alumina gas exit fitting 32 which extends vertically and is secured by ceramic cement through an aperture 80 in combustion tube 50. The open end 82 of eduction tube 30 communicates with the interior of cylindrical fitting 32 which has its upper end 83 sealed and its lower open end 84 communicating with the interior space 55 of the combustion tube for withdrawing specimen gases by the negative pressure at the input side of pump 36 (FIG. 1). Thus, opening 84 is near the enclosed end 52 of the combustion tube and draws the specimen gases from the boat 70 through baffle 62 in the direction toward the enclosed end to be educted by the eduction tube 30. The end 86 of tube 30 remote from the open end 82 extends to the end of combustion tube 50 and is coupled to slide assembly 35.

The eduction tube 30 as best seen in FIG. 2 extends parallel to the longitudinal axis of the combustion tube 50 and is spaced closely adjacent slightly above (about ¼ inch) and centered (FIG. 1) with respect to the combustion tube. It is supported in this position at end 82 by means of the exit fixture 32 and at end 86 by means of the slide assembly 35 now described in detail in conjunction with FIGS. 2 and 5.

The slide assembly 35 includes a stationary support member 85 having a concave upwardly formed recess 87 dimensioned to fit over and partially circumscribe the combustion tube 50. On the upper surface of member 85 is a downwardly projecting dovetail groove 88 for receiving a correspondingly spaced downwardly projecting dovetail slide 89 on a slide member 91 of the slide assembly 35. The stationary member 85 also includes a threaded aperture 93 extending inwardly from one end and a second aperture 95 extending downwardly through the opposite side as best seen in FIG. 5 for receiving anchor screws 97 which in turn secure opposite ends of a stainless steel strap 99 surrounding the combustion tube and securing the stationary member 85 to the top of the combustion tube as seen in FIGS. 1, 2 and 5.

The slide 91 includes a transversely extending outlet port 101 (FIG. 2) communicating with a longitudinally extending aperture 103 into which the end 86 of the eduction tube is secured. End 86 is cemented to slide member 91 by means of a cement filling aperture 105 communicating with a toroidal recess 107 circumscribing aperture 103 and permitting cement to fill around the outer circumferential boundry of the eduction tube near end 86 for securing the same within aperture 103 of slide 91. A longitudinally extending threaded clean out port 109 is also provided and communicates with aperture 103 for permitting an axially extending brush or rod to be extended into the eduction tube 30 for cleaning. Port 109 is normally plugged by means of a threaded plug 111. The dovetail groove 88 and corresponding slide 89 are machined or extruded to provide a sliding fit between slide 91 and stationary member 85 such that with relative changes in longitudinal dimensions between eduction tube 30 and combustion tube 50, slide 91 will move with respect to stationary member 85 thereby accommodating these longitudinal dimensional changes which typically are in the neighborhood of from 0.001 inches to 0.030 inches.

A conventional support bracket (not shown) is secured to the end of member 85 through threaded apertures 98 and suitable bolts for supporting in a cantilevered fashion the ends of a lance tube 90 and a flood tube 100 to the combustion tube 50 in the position shown in FIG. 2.

The combustion boat 70 is of generally conventional construction and defines an interior space 72 for receiving a specimen 75 for analysis (FIG. 3). Combustion boat 70 is made of zircon, although other high temperature ceramics could be used, and has a height sufficient to present a forward edge 74 (FIG. 2) which contacts the trailing edge of block 61 which defines a positive stop for the boat 70 thereby positioning it within the combustion zone of tube 50 when the boat is slid into the combustion tube by a suitable push rod (not shown). The height of the boat 70 also permits the boat to fit under the remaining tube structure positioned within the combustion tube.

In order to promote complete and rapid combustion of the specimen 75, an oxygen lance tube 90 is employed and has an end 92 which is fused shut. The elongated ceramic lance tube 90 is extruded of alumina and includes an opening 94 longitudinally positioned to be centered in alignment above combustion boat 70 as best seen in FIGS. 2 and 3. The end 96 of tube 90 remote from end 92 is supported as described above and extends through opening 54 and is coupled to the supply line 49 by a conventional connector. Opening 94 in tube 90 faces downwardly and is 0.1 inch in diameter for providing a gentle flow of oxygen into the open boat 70 near the end of a combustion cycle. Rotometer 48 (FIG. 1) is adjusted to provide a flow rate of approximately 1 liter per minute while rotometer 38 provides an eduction rate of 3 liters per minute.

To isolate the interior space 55 of the combustion tube from the atmosphere and thus contain the specimen gas completely within the tube, a flood tube 100 is provided and comprises a stainless steel cylindrical tube having one end 102 pinched off and thereby sealed and a plurality of projecting slots 104 cut into the walls of tube 100. The opposite end 105 of tube 100 extends outwardly through opening 54 in the combustion tube and is coupled to the oxygen supply conduit 45 for means of a suitable coupling (not shown). Flow controller 47 supplies oxygen to the flood tube 100 at a flow rate of approximately 4 liters per minute while slots to provide a curtain of oxygen flow from near the open end 54 of combustion tube 50 inwardly for about 2.0 inches. This effectively seals the combustion tube during its operation. It is noted that when pump 36 is evacuating the specimen through opening 84 in fitting 32, the pressure within the combustion tube space 55 is slightly below atmospheric pressure thus drawing an amount of the air curtain oxygen from slots 104 and tube 100 also over combustion boat 70 to further enhance the oxidation of the specimen. Tube 100, in the preferred embodiment, comprises a stainless steel tube having an inner diameter of 0.069 inch with slots 104 having a width of 0.015 inch corresponding to the kerf of the saw used to cut the slots and the space of 0.150 inch between each of the slots.

With the structure of the preferred embodiment of the invention, therefore, coal or other specimen to be analyzed is heated to a temperature of approximately 2500° F. by the resistive heating element 16 in furnace 12 (FIG. 1) while at the same time oxygen is supplied to the lance tube 90 and to the flood tube 100 both sealing the combustion tube opening 54 and providing a stream of oxygen directly into the combustion boat 70. The specimen gas resulting from the combustion of the coal and/or coke is drawn through selectively controllable baffle 62 into the open end 84 of fitting 32 and subsequently supplied to the analyzer including the infrared cell for analysis to provide a readout of the percent by weight of sulphur content contained within the coal.

Naturally, the combustion system of the present invention can be used with other substances to be analyzed and in some cases an atmosphere other than oxygen would be used for reacting with the specimen to provide combustion of the specimen into its constituent gaseous elements. These and various other modifications to the preferred embodiment will, however, fall within the spirit and scope of the present invention as defined by the appended claims.

The embodiments of the invention in which an exclusive property or privilege is claimed are defined as follows:

1. A combustion chamber for use in combusting a liquid or solid specimen into a gaseous state for subsequent analysis to determine the amount of one or more constituent elements contained in the specimen comprising:

an elongated combustion chamber continuously open at one end to receive samples to be combusted which are positioned in said chamber through said open end, said chamber enclosed at its opposite end and made of a material to withstand temperatures of combustion in excess of 3000° F., said combustion chamber including an exit port adjacent said enclosed opposite end and an area axially spaced from said exit port toward said open end for supporting a combustion boat thereon;

eduction tube means extending along and closely adjacent said combustion chamber externally thereto and having one end coupled to said exit port for communicating with the interior of said combustion chamber for withdrawing specimen gases therefrom from a position adjacent said enclosed end; and baffle means positioned in said combustion chamber between said support area for a combustion boat and said exit port and including an adjustable aperture to provide an adjustable flow path for the gaseous by-products of combustion.

2. A combustion chamber for use in combusting a liquid or solid specimen into a gaseous state for subsequent analysis to determine the amount of one or more constituent elements contained in the specimen comprising:

an elongated combustion chamber continuously open at one end to receive samples to be combusted which are positioned in said chamber through said open end, said chamber enclosed at its opposite end and made of a material to withstand temperatures of combustion in excess of 3000° F., eduction tube means extending along and closely adjacent said combustion chamber externally thereto and having one end fixedly coupled to and communicating with the interior of said combustion chamber for withdrawing specimen gases therefrom from a position closer to said enclosed end than to said open end and means for slideably securing an opposite end of said eduction tube to said combustion chamber to permit differential movement between said eduction tube and said combustion chamber, and said combustion chamber including an area for supporting a combustion boat employed for holding a sample in said combustion chamber and wherein said combustion chamber includes an exit port positioned near said enclosed end of said combustion tube and communicating with said eduction tube for removal of gaseous by-products of combustion, and further including baffle means positioned in the combustion chamber between the combustion boat and said exit port for trapping solid by-products of combustion from entering said exit port during combustion.

3. The combustion chamber defined in claim 2 wherein said baffle means includes adjustable aperture means to provide an adjustable flow path for the gaseous by-products of combustion.

4. The combustion chamber as defined in claim 3 wherein said means for slideably securing said eduction tube to said combustion chamber comprises a first member fixedly attached to said combustion chamber and having a dovetail recess extending in longitudinal alignment with the axis of said combustion chamber and a slide having a dovetail section slideable positioned within said recess and means for securing said eduction tube to said slide.

5. A combustion chamber for use in combusting a liquid or solid specimen into a gaseous state for subsequent analysis to determine the amount of one or more constituent elements contained in the specimen comprising:

an elongated combustion chamber having a length significantly greater than its width and adapted to be oriented with its longitudinal axis extending generally horizontally, said chamber being of relatively thin walled construction and continuously open at one end to receive samples to be combusted which are positioned in said chamber through said open end and enclosed at its opposite end, said combustion chamber made of a material to withstand temperatures of combustion in excess of 3000° F., said combustion chamber including an exit port adjacent said enclosed opposite end and an area axially spaced from said exit port toward said open end for supporting a combustion boat thereon;

eduction tube means extending along said combustion chamber externally thereto and having one end coupled to said exit port for communicating with the interior of said combustion chamber for withdrawing specimen gases therefrom from a adjacent said enclosed end; and baffle means positioned in said combustion chamber between said support area for a combustion boat and said exit port and including an adjustable aperture to provide an adjustable flow path for the gaseous by-products of combustion.

6. A combustion chamber for use in combusting a liquid or solid specimen into a gaseous state for subsequent analysis to determine the amount of one or more constituent elements contained in the specimen comprising:

an elongated combustion chamber having a length significantly greater than its width and adapted to be oriented with its longitudinal axis extending generally horizontally, said chamber being of relatively thin walled construction and continuously open at one end to receive samples to be combusted which are positioned in said chamber through said open end and enclosed at its opposite end, said combustion chamber made of a material to withstand temperatures of combustion in excess of 3000° F., eduction tube means extending along said combustion chamber externally thereto and having one end fixedly coupled to and communicating with the interior of said combustion chamber for withdrawing specimen gases therefrom from a position closer to said enclosed end than to said open end and an opposite end slideably secured to said combustion chamber, and said combustion chamber including an area for supporting a combustion boat employed for holding a sample in said combustion chamber and wherein said combustion chamber includes an exit port positioned near said enclosed end of said combustion tube and communicating with said eduction tube for removal of gaseous by-products of combustion, and further including baffle means positioned in the combustion chamber between the combustion boat and the exit port for trapping solid by-products of combustion from entering said exit port during combustion.

7. The combustion chamber as defined in claim 6 wherein said combustion chamber comprises a cylindrical member having an enclosed end opposite said open end.

8. The combustion chamber as defined in claim 7 wherein said combustion chamber is made of a ceramic material.

9. The combustion chamber as defined in claim 8 wherein said combustion chamber is cut away at said open end to provide a pair of spaced horizontally extending ledges extending from said open end.

10. The combustion chamber as defined in claim 9 wherein said ceramic material comprises alumina.

11. The combustion chamber as defined in claim 10 and further including lance means positioned in said combustion chamber for directing a reactive gas into said combustion chamber above a combustion boat positioned on said support area therefor to facilitate combustion of the specimen.

12. The combustion chamber as defined in claim 11 and further including means for providing a sealing curtain of gas at said open end of said combustion chamber.

* * * * *

UNITED STATES PATENT AND TRADEMARK OFFICE
CERTIFICATE OF CORRECTION

PATENT NO. : 4,352,781
DATED : October 5, 1982
INVENTOR(S) : Larry O'Brien

It is certified that error appears in the above—identified patent and that said Letters Patent is hereby corrected as shown below:

Column 5, line 59:

"boundry" should be --boundary--

Column 8, line 30:

"slideable" should be --slideably--

Column 8, line 57:

"a" should be --an--

Signed and Sealed this

Eleventh Day of January 1983

[SEAL]

Attest:

GERALD J. MOSSINGHOFF

Attesting Officer     Commissioner of Patents and Trademarks